(12) United States Patent
Wang et al.

(10) Patent No.: US 11,235,083 B2
(45) Date of Patent: Feb. 1, 2022

(54) COMPOSITE HYDROGEL AND METAL SILICATE WOUND HEALING MATERIAL

(71) Applicant: MLK BIOSCIENCE CO., LTD., Taoyuan (TW)

(72) Inventors: Wan-Ting Wang, New Taipei (TW); Yeh-Shiu Chu, New Taipei (TW)

(73) Assignee: MLK BIOSCIENCE CO., LTD., Taoyuan (TW)

( * ) Notice: Subject to any disclaimer, the term of this patent is extended or adjusted under 35 U.S.C. 154(b) by 0 days.

(21) Appl. No.: 16/605,498

(22) PCT Filed: Jan. 24, 2018

(86) PCT No.: PCT/CN2018/074042
§ 371 (c)(1),
(2) Date: Nov. 13, 2019

(87) PCT Pub. No.: WO2018/192285
PCT Pub. Date: Oct. 25, 2018

(65) Prior Publication Data
US 2020/0114039 A1 Apr. 16, 2020

(30) Foreign Application Priority Data
Apr. 17, 2017 (CN) .................... CN201710248691.0

(51) Int. Cl.
*A61L 15/60* (2006.01)
*A61L 15/24* (2006.01)
(Continued)

(52) U.S. Cl.
CPC ............... *A61L 15/60* (2013.01); *A61L 15/24* (2013.01); *A61L 15/325* (2013.01); *A61L 15/44* (2013.01);
(Continued)

(58) Field of Classification Search
CPC .......... A61L 15/22; A61L 15/42; A61L 15/26; A61L 15/325; A61L 15/20;
(Continued)

(56) References Cited

U.S. PATENT DOCUMENTS

2006/0182788 A1* 8/2006 Singh ...................... A61L 15/44
424/448
2011/0001087 A1* 1/2011 Hillebrecht ............. A61L 15/60
252/194

(Continued)

OTHER PUBLICATIONS

Dhivya et al, title: wound dressings—a review, BioMedicine, vol. 5, No. 4, Article 4, pp. 24-28; published Dec. 2015. (Year: 2015).*
(Continued)

*Primary Examiner* — Carlos A Azpuru
(74) *Attorney, Agent, or Firm* — Hannah Tien

(57) ABSTRACT

Disclosed is a hydrophilic dressing (200) having appropriate mechanical strength, comprising a composite material (100, 220) and a film (210). The composite material (100, 220) comprises a hydrophilic substrate material (110) and a compound (120) that promotes wound healing, wherein the hydrophilic substrate material (110) is a reaction product of a hydrophilic polymer, wherein the hydrophilic polymer comprises a hydrophilic monomer, a cross-linking agent and an inorganic silicon-oxygen compound, wherein the compound (120) that promotes wound healing is distributed in the hydrophilic substrate material (110).

9 Claims, 1 Drawing Sheet

(51) Int. Cl.
  *A61L 15/32* (2006.01)
  *A61L 15/44* (2006.01)
  *C08F 220/58* (2006.01)

(52) U.S. Cl.
  CPC ..... *C08F 220/585* (2020.02); *A61L 2300/252* (2013.01); *A61L 2300/412* (2013.01)

(58) Field of Classification Search
  CPC ......... A61L 2300/252; A61L 2300/412; A61L 15/60; A61L 26/252; A61L 2300/404; A61L 2300/414; A61L 26/0004; A61L 26/0014; C08F 220/58; C08F 222/38; C08F 220/56; C08F 220/585
  See application file for complete search history.

(56) References Cited

U.S. PATENT DOCUMENTS

2014/0371692 A1* 12/2014 Cleary .................... A61L 15/44
  604/307
2016/0175488 A1*  6/2016 Klein ........................ C08F 2/44
  523/113

OTHER PUBLICATIONS

Unknown author, title: The Difference Between DE and Bentonite Clay, product information from https://www.americanelements.com/bentonite-1302-78-9. Downloaded Jul. 9, 2020 (Year: 2020).*

* cited by examiner

COMPOSITE HYDROGEL AND METAL SILICATE WOUND HEALING MATERIAL

TECHNICAL FILED

The present invention relates to a composite material, the composite material is a solid hydrophilic polymer with a strong three-dimensional network structure comprising a compound that promotes wound healing.

BACKGROUND OF THE INVENTION

In the past, keeping a wound dry was the main principle of wound care, and dry gauze dressings were therefore used to protect the wound. However, the gauze often stick to the wound, causing secondary harms and pains to the wound that has just been healed when the dressing was removed. In recent years, studies have shown that keeping a wound moist would facilitate the movement and proliferation of epidermal cells, and accelerate wound healing, therefore a variety of wet dressings have been introduced, for example, hydrocolloid dressings and hydrogel dressings.

However, the moisture content of hydrocolloid dressings is <10%. When a hydrocolloid dressing is applied when there is few exudate, it tends to make the wound dry cause pain, and cannot keep the wound moist. Furthermore, it is mainly made of carboxymethyl cellulose, which can be easily decomposed by bacteria which infects the wound and produce foul odor. Therefore, hydrocolloids cannot be used on infected wounds.

There are water-swellable hydrogels, which the mechanical strength of current products is however not as desired, for example, Taiwan Patent No. M419555, 1267387, 1429462, and 1504420; Chinese Patent No. CN204863670 and US Patent Publication No. 2013/0072843, which disclose hydrogels combined with nonwoven fabric or fiber as a support layer to strengthen the structure; however, the structure of the hydrogels after being swelled by absorbing aqueous solution is still fragile, resulting in fragmented residual gels that are difficult to remove when the dressing is to be removed.

Generally, in order to accelerate healing of chronic wounds, in addition to dressings that keep the wound moist and isolate external harms, wound-healing promoting factors are also necessary. For example, U.S. Pat. Nos. 5,489,304 and 5,716,411 disclose mixing collagen-glycosaminoglycan to cover the surface of a wound, and then coating a layer of cultured animal or human epidermal cells to promote skin regeneration. U.S. Pat. No. 5,977,088 discloses a pharmaceutical composition comprising a pharmaceutical agent for treating or alleviating skin diseases and hyaluronic acid, the pharmaceutical composition utilizes hyaluronic acid to promote or trigger delivery of the pharmaceutical agent to the skin of a wounded individual, it can also accumulate and prolong the stay of the pharmaceutical agent at the site.

However, the effective factors or wet dressings that accelerate wound healing described above require two steps while applying, which includes coating with effective factors first and then covering with the dressings for protection, making a care process cumbersome; furthermore, when wound-healing promoting factors are excessively applied, it is wasteful and the dressing tends to be poorly adhered. Although the Taiwan Patent No. 1264306 discloses a gauze dressing coated with a collagen-hyaluronic acid mixture, it is a composite material of dry gauze, which is not good for wound healing.

Therefore, how to effectively combine effective factors that accelerate wound healing with wet dressing to strengthen wound care and healing is a problem that needs to be solved in the industry.

DETAILED DESCRIPTION OF THE INVENTION

In view of the above, the present invention provides a hydrophilic dressing having suitable mechanical strength, which comprises a composite material and a film, most particularly the composite material is composed of a hydrophilic polymer and a compound that promotes wound healing. The hydrophilic polymer is a polymer with strong structure and hydrophilicity; therefore, the hydrophilic polymer not only keeps a wound moist, but also accelerates the movement and proliferation of epidermal cells. Due to the hydrophilic polymer is a solid hydrophilic polymer having a strong three-dimensional network structure, the problem with hydrogel, which is prone to breakage when being swelled after absorbing aqueous solution, has been overcome. In addition, the hydrophilic polymer utilizes its hydrophilic groups' absorptivity to adsorb a compound that promotes wound healing, such as water-soluble collagen or hyaluronic acid, to the three-dimensional network structure inside the hydrophilic polymer, allowing wound-healing promoting factors to be slowly released during wound treatment to accelerate wound healing. Furthermore, in current wound treatment, a wounded individual is treated by applying a wound healing compound first, and then covering the wound with a dressing, which requires two steps. However, the hydrophilic dressing of the present invention can achieve the above-described treatment goal by one step, effectively shortening the time required for wound healing.

To achieve the goal described above, the present invention provides a composite material, which comprises a hydrophilic substrate and a compound that promotes wound healing, wherein the hydrophilic substrate is a reaction product of a hydrophilic polymer, wherein the hydrophilic polymer comprises a hydrophilic monomer, a crosslinking agent, and an inorganic silicon-oxygen compound, wherein the compound that promotes wound healing is distributed in the hydrophilic substrate.

The term "a" or "an" as used herein is to describe elements and components of the present invention. This term is merely used to conveniently describe and provide the basic concept of the present invention. The description should be understood as comprising one or at least one, and unless otherwise explicitly indicated by the context, singular terms include pluralities and plural terms include the singular. When used in conjunction with the word "comprising" in a claim, the term "a" or "an" may mean one or more than one.

The term "or" used herein refers to "and/or" unless substitutes are mutually exclusive.

The term "hydrophilic monomer" as used herein includes a reactive monomer having a hydrophilic group. The hydrophilic monomer used in preparing a hydrophilic polymer of the present invention has at least one polymerizable double bond and at least one hydrophilic functional group. Examples of the functional group having a polymerizable double bond include: double bonds of acrylic acid, methacrylic acid, acrylamide group, methacrylamide group, fumaric acid, maleic acid, styryl group, isopropenylphenyl group, O-ethylene carbonate, O-vinyl urethane, allyl group, O-vinyl acetyl group, and N-vinyl lactam, and N-vinyl amido.

Types of hydrophilic monomers suitable for the present invention include monomers containing acrylic acid or vinyl groups. The term "acrylic acid" or "acrylic acid-containing" monomers are monomers comprising the following acrylic group: ($CH_2$=CRCOX), wherein R is H or $CH_3$, and X is O or N, which are also known as monomers capable of undergoing rapid polymerization, for example, N,N-dimethylacrylamide (DMA), 2-hydroxyethyl methacrylate (HEMA), glyceryl methacrylate, 2-hydroxyethylmethacrylamide, polyethylene glycol methacrylate, methacrylic acid, mixtures thereof and the likes. The term "vinyl" or "vinyl-containing" monomers refer to monomers having a vinyl group (—CH=$CH_2$) and capable of undergoing polymerization. Vinyl containing monomers include, but are not limited to, monomers such as N-vinyl amide, N-vinyl lactam (for example, NVP), N-vinyl-N-methylacetamide, N-vinyl-N-ethylacetamide, N-vinyl-N-ethylformamide, N-vinylformamide.

Other hydrophilic monomers that can be used in the present invention include, but are not limited to, polyoxyethylene polyols having one or more terminal hydroxyl groups substituted with a functional group containing a polymerizable double bond. Examples include polyethylene glycol, ethoxylated alkyl glucosides and ethoxylated bisphenol A, which react with one or more molar equivalent of end-capping groups, such as isocyanatoethyl methacrylate (IEM), methacrylic anhydride, methacryloyl chloride, vinyl benzoyl chloride or the likes, to produce polyethyl polyol having one or more terminal polymerizable alkenyl groups, and the one or more terminal polymerizable alkenyl groups are bonded to the polyethyl polyol via a linking moiety, such as urethane or an ester group.

The hydrophilic monomer of the present invention may be any hydrophilic monomer known to be useful in the manufacture of hydrogels. In one embodiment, the hydrophilic monomer comprises acrylic acid having a double bond or a derivative thereof, acrylamide or a derivative thereof, 2-acrylamido-2-methylpropane sulfonic acid or a salt thereof, polyethylene glycol or a derivative thereof or a combination thereof.

In another embodiment, the hydrophilic monomer is from 8 to 80% by weight based on the weight of the hydrophilic polymer. In a preferred embodiment, the hydrophilic monomer is from 10 to 50% by weight based on the weight of the hydrophilic polymer.

The crosslinking agent of the present invention is not particularly limited as long as it can react with a functional group of the hydrophilic polymer to initiate a crosslinking reaction. As used herein, a "crosslinking agent" includes, but is not limited to, a compound having at least two ethylenically unsaturated groups. In one embodiment, the crosslinking agent includes N,N'-methylenebisacrylamide, ethylene glycol dimethacrylate, polyethylene glycol diacrylate, tetraethylene glycol dimethacrylate, triethylene glycol dimethacrylate, polyethylene glycol dimethacrylate, trimethylpropanetrimethacrylate, ethylene methacrylate, ethylenediamine dimethyl acrylamide, glycerol dimethacrylate, diethylene glycol dimethacrylate, divinyl benzene or a combination thereof.

In another embodiment, the crosslinking agent is from 0.1 to 20% by weight based on the weight of the hydrophilic polymer. In a preferred embodiment, the crosslinking agent is from 0.2 to 10% by weight based on the weight of the hydrophilic polymer. In a more preferred embodiment, the crosslinking agent is from 0.5 to 5% by weight based on the weight of the hydrophilic polymer.

The present invention increases the strength of the reaction product (i.e., the hydrophilic substrate) of the hydrophilic polymer by adding an inorganic silicon-oxygen compound to the hydrophilic polymer. The hydrophilic substrate has a strong three-dimensional network structure, so that the situation that the structure of the hydrogel that is prone to breakage when being swelled by absorbing aqueous solution is overcome. In one embodiment, the inorganic silicon-oxygen compound is a compound having a silicon-oxygen chain as the main chain. The basic structural unit of the silicon-oxygen chain is composed of a silicon-oxygen bond having a reactive group capable of chemically bonding with an inorganic material, and capable of chemically bonding with an organic material. Therefore, the structure of the inorganic silicon-oxygen compound has the ability of bonding "organic groups" and contains an "inorganic structure." Because of this special composition and the structure of reactive groups, when being reacted with an organic polymerizing monomer, an coupling reaction can be initiated by its special physical and chemical properties, effectively improving the mechanical strength, water resistance, cold resistance and adhesion of the polymeric material.

The inorganic silicon-oxygen compound of the present invention comprises an inorganic silicate. The inorganic silicate refers to a compound composed of silicon and oxygen ($Si_xO_y$), which can be represented by a salt produced from silicon oxide or silicic acid. In one embodiment, the inorganic silicon-oxygen compound is silicon oxide or a metal silicate. The term "metal silicate" as used herein is a generic term for compounds composed of silicon, oxygen and metal elements. The metal silicate means that the silicon-oxygen bond silicon oxide is substituted with a metal salt, and the particle diameter of the produced metal silicate is small, the specific surface area is large, the original single particle is 0.02 μm, the aggregated particles is 5 μm, the assembled particles is 30 μm, and the specific surface area is 20-800 $m^2$/g. When the specific surface area of the metal silicate is more than 50 $m^2$/g, silanol groups on the surface cause interaction between the particles, when being used as a filler of a hydrophobic plastic polymer such as rubber or plastic, the plastic is imparted with an excellent reinforcing effect. In a preferred embodiment, the metal silicate is magnesium aluminum silicate.

The specific surface area of a particle refers to the total surface area of a unit mass (or volume) of a particulate material, which can be used as one of important parameters for evaluating the performance of a catalyst, an adsorbent, and other porous materials. Therefore, when the specific surface area of a particle is increased, the adsorption area thereof can be increased, thereby increasing the adsorption capacity. In one embodiment, the specific surface area of a particle of the inorganic silicon-oxygen compound is greater than 50 $m^2$/g. In a preferred embodiment, the specific surface area of a particle of the inorganic silicon-oxygen compound is greater than 100 $m^2$/g. In a more preferred embodiment, the specific surface area of a particle of the inorganic silicon-oxygen compound is greater than 150 $m^2$/g.

In another embodiment, the inorganic silicon-oxygen compound is from 2 to 80% by weight based on the weight of the hydrophilic polymer. In a preferred embodiment, the inorganic silicon-oxygen compound is from 4 to 50% by weight based on the weight of the hydrophilic polymer. In a more preferred embodiment, the inorganic silicon-oxygen compound is from 6 to 40% by weight based on the weight of the hydrophilic polymer.

In one embodiment, the inorganic silicon-oxygen compound is an inorganic compound having a silicon-oxygen tetrahedral structure or a polysilicon-oxygen tetrahedral structure. Therefore, the strength of the hydrophilic polymer can be improved by polymerizing the inorganic silicon-oxygen compound into a three-dimensional network structure in the hydrophilic polymer.

The hydrophilic polymer further comprises one or more polymerization initiators. The polymerization initiator is used in an effective amount in the hydrophilic polymer to initiate photopolymerization of the hydrophilic polymer. The polymerization of the hydrophilic polymer can be initiated by heat, visible light, ultraviolet light or other suitable options depending on the polymerization initiator that is used. Alternatively, it can be initiated without a photoinitiator, for example using an electron beam (e-beam).

Examples of the polymerization initiator include, but are not limited to, lauryl peroxide, benzoyl peroxide, isopropyl peroxycarbonate, azobisisobutyronitrile, and the likes, which will generate free radicals at a moderately elevated temperature, as well as photoinitiator systems such as aromatic alpha-hydroxy ketone, alkoxy benzoin, acetophenone, acylphosphine oxide, bisacylphosphine oxide and tertiary amine plus diketone, a mixture thereof and the likes. The UV photopolymerization initiator includes Irgacure 1173 and Irgacure 2959 (Ciba Specialty Chemicals).

Therefore, the polymerization initiator can facilitate polymerization reaction of other components of the hydrophilic polymer with one another to obtain a reaction product of the hydrophilic polymer as the hydrophilic substrate.

After the hydrophilic substrate is cured, the composite material is formed by adsorbing water-soluble wound healing promoting factors to a three-dimensional network structure inside the hydrophilic substrate by using its hydrophilic group having adsorptivity. Therefore, when the composite material is made into a hydrophilic dressing and attached to a wound, the wound healing promoting factors are released from the composite material to accelerate wound healing.

Furthermore, in one embodiment, the water content of the hydrophilic substrate is >40%. In a preferred embodiment, the water content of the hydrophilic substrate is >50%. In a more preferred embodiment, the water content of the hydrophilic substrate is >60%. Therefore, the water content of the hydrophilic substrate of the present invention is high, and when the composite material is made into a hydrophilic dressing and adhered to a wound, it can keep the wound moist, and reduce discomfort caused by the wound to a wounded individual.

The term "wound" as used herein may be open wounds and closed wounds. Open wounds may be divided into many categories, including cuts (caused by clean, sharp objects such as knives or razors), cracks (rough irregular wounds caused by pressure or tear), and scratches (usually superficial wounds caused by sliding over rough surfaces, only the uppermost skin is rubbed off), and stab wounds (caused by an object such as a nail or needle piercing the skin). The categories of closed wounds are much less, but they are as dangerous as open wounds. They are contusions or injuries (damages to subcutaneous tissues caused by physical forces), hematoma (blood accumulation under the skin caused by damages to blood vessels), and crushes (due to application of long or large external forces).

The term "compound that promotes wound healing" as used herein includes, but is not limited to, a compound having an effect of promoting wound healing. In one embodiment, the compound that promotes wound healing comprises a water soluble compound that promotes wound healing. In a preferred embodiment, the compound that promotes wound healing comprises a wound healing promoting factor. In a more preferred embodiment, the compound that promotes wound healing comprises collagen, hyaluronic acid, gelatin, a growth factor, a cytokine, an alginate, silver ions, chitosan or a combination thereof. The term "cytokine" as used herein includes, but is not limited to, interleukins and interferons. The term "growth factor" as used herein includes but is not limited to epidermal growth factor (EFG), fibroblast growth factor (FGF), vascular endothelial growth factor (VEGF), connective tissue growth factor, platelet-derived growth factor (PDGF), insulin-like growth factor, nerve growth factor, colony-stimulating factor, stem call factor, keratinocyte growth factor, granulocyte colony-stimulating factor, granulocyte macrophage colony-stimulating factor, glial-derived neurotropic factor, endothelial-monocyte activating polypeptide, epithelial neutrophil activating peptide, erythropoietin, BRAK, transforming growth factor-$\beta$.

In another embodiment, the compound that promotes wound healing is from 0.01 to 20% based on the total weight of the hydrophilic polymer. In a preferred embodiment, the compound that promotes wound healing is from 0.05 to 18% based on the total weight of the hydrophilic polymer. In a more preferred embodiment, the compound that promotes wound healing is from 0.1 to 15% based on the total weight of the hydrophilic polymer.

The composite material of the present invention is further bonded with a film so as to form a hydrophilic dressing. In one embodiment, the film has a two-sided structure, wherein one side is a bonding surface which is bonded with the composite material. In another embodiment, the film is a film having the effect of water resistant and air permeable. In a preferred embodiment, the film is a polyurethane (PU) film.

In one embodiment, the surface area of the film is greater than the surface area of the composite material. Therefore, the bonding surface of the film has a bonding area, in addition to the area for bonding the composite material, for bonding the hydrophilic dressing with the skin. In another embodiment, the bonding surface is an acrylic adhesive bonding surface. The acrylic adhesive bonding surface is used to bond the composite material and the skin of a subject.

The present invention also provides a method for preparing a composite material, comprising the steps of: (1) crosslinking and polymerizing a hydrophilic polymer to obtain a hydrophilic substrate, wherein the hydrophilic polymer comprises a hydrophilic monomer, a crosslinking agent, and an inorganic silicon-oxygen compound; and (2) adding a compound that promotes wound healing to the hydrophilic substrate to obtain the composite material, wherein the compound that promotes wound healing is adsorbed by the hydrophilic substrate and distributed in the hydrophilic substrate.

In one embodiment, the hydrophilic monomer comprises acrylic acid having a double bond or a derivative thereof, acrylamide or a derivative thereof, 2-acrylamido-2-methylpropane sulfonic acid or a salt thereof, polyethylene glycol or a derivative thereof or a combination thereof.

In another embodiment, the hydrophilic monomer is from 8 to 80% by weight based on the weight of the hydrophilic polymer. In a preferred embodiment, the hydrophilic monomer is from 10 to 50% by weight based on the weight of the hydrophilic polymer.

In one embodiment, the crosslinking agent includes N,N'-methylenebisacrylamide, ethylene glycol dimethacrylate, polyethylene glycol diacrylate, tetraethylene glycol dimethacrylate, triethylene glycol dimethacrylate, polyethylene glycol dimethacrylate, trimethylpropanetrimethacrylate, ethylene methacrylate, ethylenediamine dimethyl acrylamide, glycerol dimethacrylate, diethylene glycol dimethacrylate, divinyl benzene or a combination thereof.

In another embodiment, the crosslinking agent is from 0.1 to 20% by weight based on the weight of the hydrophilic polymer. In a preferred embodiment, the crosslinking agent is from 0.2 to 10% by weight based on the weight of the hydrophilic polymer. In a more preferred embodiment, the crosslinking agent is from 0.5 to 5% by weight based on the weight of the hydrophilic polymer.

In one embodiment, the inorganic silicon-oxygen compound comprises an inorganic silicate. In a preferred embodiment, the inorganic silicon-oxygen compound is silicon oxide or a metal silicate. In a more preferred embodiment, the metal silicate is magnesium aluminum silicate.

In another embodiment, the inorganic silicon-oxygen compound is an inorganic compound having a silicon-oxygen tetrahedral structure or a polysilicon-oxygen tetrahedral structure. In another embodiment, the specific surface area of a particle of the inorganic silicon-oxygen compound is greater than 50 $m^2/g$. In a preferred embodiment, the specific surface area of a particle of the inorganic silicon-oxygen compound is greater than 100 $m^2/g$. In a more preferred embodiment, the specific surface area of a particle of the inorganic silicon-oxygen compound is greater than 150 $m^2/g$.

In one embodiment, the inorganic silicon-oxygen compound is from 2 to 80% by weight based on the weight of the hydrophilic polymer. In a preferred embodiment, the inorganic silicon-oxygen compound is from 4 to 50% by weight based on the weight of the hydrophilic polymer. In a more preferred embodiment, the inorganic silicon-oxygen compound is from 6 to 40% by weight based on the weight of the hydrophilic polymer.

The hydrophilic polymer of the step (1) in the preparation method of the present invention further comprises a polymerization initiator. The polymerization initiator is used in an effective amount in the hydrophilic polymer to initiate photopolymerization of the hydrophilic polymer. Examples of the polymerization initiator include, but are not limited to, lauryl peroxide, benzoyl peroxide, isopropyl peroxycarbonate, azobisisobutyronitrile, and the likes, which will generate free radicals at a moderately elevated temperature, as well as photoinitiator systems such as aromatic alpha-hydroxy ketone, alkoxy benzoin, acetophenone, acylphosphine oxide, bisacylphosphine oxide and tertiary amine plus diketone, a mixture thereof and the likes. In one embodiment, the polymerization initiator is an UV photopolymerization initiator. The UV photopolymerization initiator initiates a polymerization reaction by using UV light irradiation. In a preferred embodiment, the UV photopolymerization initiator is Irgacure 1173 or Irgacure 2959.

In one embodiment, the method for crosslinking and polymerizing the hydrophilic polymer includes heating, visible light or ultraviolet light in order to cause crosslinking and polymerization of the hydrophilic polymer.

In another embodiment, the compound that promotes wound healing includes a water soluble compound that promotes wound healing. In a preferred embodiment, the compound that promotes wound healing comprises collagen, hyaluronic acid, gelatin, a growth factor, a cytokine, an alginate, silver ions, chitosan or a combination thereof.

In one embodiment, the compound that promotes wound healing is from 0.01 to 20% based on the total weight of the hydrophilic polymer. In a preferred embodiment, the compound that promotes wound healing is from 0.05 to 18% based on the total weight of the hydrophilic polymer. In a more preferred embodiment, the compound that promotes wound healing is from 0.1 to 15% based on the total weight of the hydrophilic polymer.

Because the hydrophilic substrate has hydrophilic groups, it can adsorb the compound that promotes wound healing; and because the hydrophilic substrate is a solid hydrophilic polymer with a three-dimensional network structure, the three-dimensional network structure can slowly release the compound that promotes wound healing to strengthen the wound healing effect of the composite material.

The composite material prepared by the present invention can be further bonded with a film so as to obtain a hydrophilic dressing used for wound healing.

The film of the present invention is waterproof, transparent and air permeable; accordingly, it not only can prevent water or bacteria from entering into the hydrophilic dressing, but also can maintain excellent air permeability. In one embodiment, the film is a film having the effect of waterproofing and air-permeable. In a preferred embodiment, the air-permeable film layer can be made of polyurethane (PU).

Furthermore, the film of the present invention is a film having a single-sided adhesive which, in addition to bonding with the composite material, also bonds with the skin of a subject. Therefore, in one embodiment, the film has a two-sided structure, wherein one side is a bonding surface, and the bonding surface is bonded with the composite material. In a preferred embodiment, the bonding surface is an acrylic adhesive bonding surface. The acrylic adhesive bonding surface is used to bond the composite material and the skin of a subject. In another embodiment, the surface area of the film is greater than the surface area of the composite material. Therefore, the bonding surface of the film has a bonding area, in addition to the bonding area that bonds with the composite material, for bonding the hydrophilic dressing and the skin of a subject; and the skin bonding area is a sealed environment for oxygen supply and moisture exchange, isolating microorganisms and contaminants from entering into the wound and keeping the wound in a moist condition, not excessively wet or dry.

In one embodiment, the subject is an animal, preferably a mammal, and more preferably a human.

The present invention further provides a hydrogel structure which comprises a hydrophilic substrate layer and a plurality of molecular particles, wherein the hydrophilic substrate layer is composed of a hydrophilic polymer, wherein the hydrophilic polymer comprises a hydrophilic monomer, a crosslinking agent and an inorganic silicon-oxygen compound, wherein the plurality of molecular particles is distributed in the hydrophilic substrate layer, wherein each of the plurality of molecular particles is a compound that promotes wound healing.

In one embodiment, the hydrophilic substrate layer has a three-dimensional network structure, and the plurality of molecular particles adhere to the three-dimensional network structure.

In another embodiment, the plurality of molecular particles are in the shape of a sphere.

In one embodiment, the hydrophilic monomer comprises acrylic acid having a double bond or a derivative thereof, acrylamide or a derivative thereof, and 2-acrylamido-2-methylpropane sulfonic acid or a salt thereof, polyethylene glycol or a derivative thereof, or a combination thereof.

In another embodiment, the crosslinking agent includes N,N'-methylenebisacrylamide, ethylene glycol dimethacrylate, polyethylene glycol diacrylate, tetraethylene glycol dimethacrylate, triethylene glycol dimethacrylate, polyethylene glycol dimethacrylate, trimethylpropanetrimethacrylate, ethylene methacrylate, ethylenediamine dimethyl acrylamide, glycerol dimethacrylate, diethylene glycol dimethacrylate, divinyl benzene or a combination thereof. In one embodiment, the inorganic silicon-oxygen compound is an inorganic compound having a silicon-oxygen tetrahedral structure or a polysilicon-oxygen tetrahedral structure.

In another embodiment, the hydrophilic polymer further comprises a polymerization initiator. In a preferred embodiment, the polymerization initiator is Irgacure 2959.

In one embodiment, the compound that promotes wound healing comprises collagen, hyaluronic acid, gelatin, a growth factor, a cytokine, an alginate, silver ions, chitosan or a combination thereof.

In another embodiment, the hydrogel structure is further bonded with a film layer disposed above the hydrogel structure, and the surface area of the film layer is greater than the surface area of the hydrogel structure. In a preferred embodiment, the film layer has a two-sided structure, wherein one side is a bonding surface, the bonding surface is bonded with the hydrogel structure. In a more preferred embodiment, the film layer is made of a polyurethane (PU).

Accordingly, the primary goal of the present invention is to provide a solid hydrophilic polymer having an appropriate strength, elasticity and a three-dimensional network structure. The hydrophilic polymer has a hydrophilic group, therefore it has hygroscopic and anti-hydrolysis properties, can absorb wound exudate and keep the wound moist; and the three-dimensional network solid structure having appropriate strength covers the wound, not only to isolate the external environment to protect the wound, but also accelerate the proliferation and movement of epidermal cells of the wound, thereby accelerating wound healing.

Another goal of the present invention is to provide a solid hydrophilic polymer having appropriate strength, which does not require non-woven fabric or fiber as a support layer to strengthen its structure, and utilizes its hydrophilic groups to adsorb wound healing promoting factors, and the three-dimensional network structure in the hydrophilic polymer is used to achieve the effect of sustained release of wound healing promoting factors, thereby accelerating wound healing.

BRIEF DESCRIPTION OF THE INVENTION

EXAMPLES

The following examples are non-limiting and merely represent several aspects and features of the present invention.

The present invention is to form a water-insoluble, high-strength solid hydrophilic polymer by curing and polymerizing a reactive monomer having a hydrophilic group, a crosslinking agent and a compound having a silicon-oxygen tetrahedral structure, and then to utilize the absorptivity of the hydrophilic group of the hydrophilic polymer substrate itself to adsorb a wound healing effective factor in the hydrophilic polymer having a solid three-dimensional network structure.

Example 1

Preparation of Hydrophilic Polymer 3 g of acrylamide (a hydrophilic monomer), 7 g of 2-acrylamido-2-methylpropanesulfonic acid (a hydrophilic monomer), 2 g of silicon oxide, N,N'-methylenebisacrylamide (the added amount was 1% by weight based on the total weight of the hydrophilic polymer) (a crosslinking agent) were mixed with water to 100 g, and stirred well.

After oxygen was removed from the above solution, an initiator Irgacure 2959 (the added amount was 2% by weight based on the total weight of the hydrophilic polymer) was added to the solution and stirred well. The solution was transferred to a reaction mold, and irradiated under the ultraviolet light to cause the solution in the reaction mold to start undergoing cross-linking polymerization, and the liquid oligomers in the solution gradually formed a hydrophilic polymer having a water insoluble solid three-dimensional network structure as a hydrophilic substrate.

Example 2

Preparation of Composite Material 10 grams of a 10% collagen solution was added, which was a wound healing effective factor, in the above solid hydrophilic polymer. After the solid hydrophilic polymer completely adsorbed the collagen solution, a composite material could thus be obtained.

Figure 1:
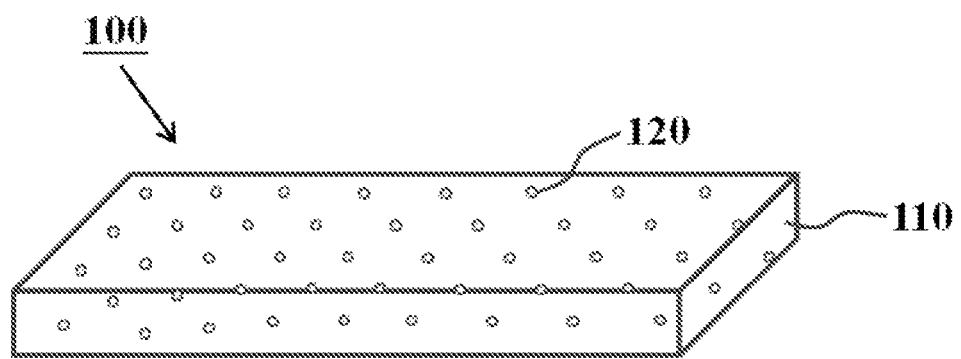
FIG. 1 is a schematic diagram showing the structure of the composite material of the present invention.

As shown in FIG. 1, it is a schematic diagram showing the structure of the composite material 100 of the present invention, the composite material 100 comprised a hydrophilic substrate 110 and a wound healing effective factor 120. The hydrophilic substrate 110 was a reaction product of a hydrophilic polymer, which was a solid material having a three-dimensional network structure, wherein the hydrophilic polymer comprised a hydrophilic monomer, a crosslinking agent and an inorganic silicon-oxygen compound. The wound healing effective factor 120 was distributed in the three-dimensional network structure of the hydrophilic substrate 110; when the composite material 100 was used for treating a wound, the wound healing effective factor 120 was able to be released in the composite material 100 to accelerate wound healing. One embodiment of the wound healing effective factor 120 was collagen.

Example 3

Efficacy Test of Composite Materials

According to the above preparation method of the composite material of the present invention, only the added amount of the silicon oxide portion in the hydrophilic polymer was adjusted or silicon oxide was replaced with other components, that was, the components and the added amount of the original 3 g of acrylamide, 7 g of 2-acrylamido-2-methylpropane sulfonic acid and N,N'-methylenebisacrylamide (the added amount was 1% based on the total weight of the hydrophilic polymer) remained the same to prepare samples of four different composite materials. The differences in the preparation method of each sample were as follows: Sample 1: the added amount of silicon oxide was 2 g; sample 2: the added amount of silicon oxide was 6 g; sample 3: silicon oxide was replaced with magnesium aluminum silicate, and the added amount was 2 g; and sample 4: silicon oxide was replaced with magnesium aluminum silicate, and the added amount was 6 g.

The above four composite materials samples of different ratios were compared with commercially available hydrogel dressings (as the comparison group), the mechanical properties of the composite materials before being immersed in physiological saline solution and after being immersed and fully swelled were measured. The measurement results are shown in Table 1.

TABLE 1

Measurement results of the samples of 4 composite materials of the present invention compared to the comparison group

|  |  | Sample 1 | Sample 2 | Sample 3 | Sample 4 | Comparison group |
|---|---|---|---|---|---|---|
| Compression strength (KPa) | swelling condition before immersion | 12 | 30 | 16 | 50 | 40 |
|  | swelling condition after immersion | 5 | 15 | 10 | 30 | Broken |
| Elongation ratio (%) | swelling condition before immersion | 120 | 310 | 130 | 360 | 150 |
|  | swelling condition after immersion | 110 | 170 | 115 | 190 | Broken |

Example 4

Preparation of Hydrophilic Dressing

A film having a single-sided adhesive (for example, a commercially available "SuFuTe" which was waterproof and air permeable coating) was bonded with the composite material, i.e., the side of the film that had the adhesive was bonded with the composite material to form a hydrophilic dressing.

Figure 2:
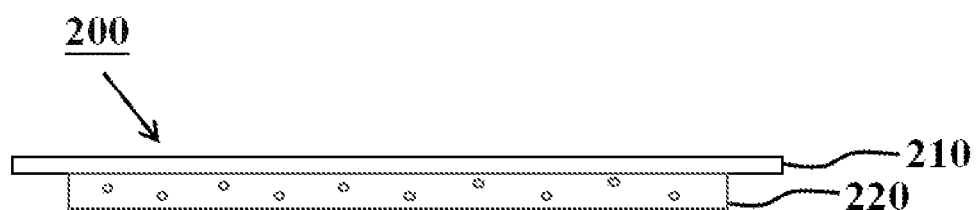
FIG. 2 is a schematic diagram showing the side view of the structure of the hydrophilic dressing of the present invention; in which 100, 220: composite material; 110: hydrophilic substrate; 120: wound healing effective factor; 200: hydrophilic dressing; 210: film.

As shown in FIG. 2, which was a schematic diagram showing the side view of the structure of the hydrophilic dressing 200 of the present invention. The hydrophilic dressing 200 comprised a film 210 and a composite material 220, wherein the film 210 was disposed on the composite material 220. The film 210 had a two-sided structure, wherein one side was a bonding surface (not shown), the bonding surface had an adhesive thereon, and the bonding surface was bonded with the composite material 220, so that the hydrophilic dressing 200 was composed of the film 210 and the composite material 220. Further, the surface area of the film 210 was greater than the surface area of the composite material 220. Therefore, the bonding surface of the film 210 had a bonding area, in addition to the bonding area for bonding with the composition material 220, for bonding the hydrophilic dressing 200 with the skin of a subject. The skin bonding area was a sealed environment for oxygen supply and moisture exchange, which insulated microorganisms and contaminants from entering into the wound so as to keep the wound in a moist condition, without being excessively wet or excessively dry.

The above examples are merely illustrative of the effects of the present invention and are illustrative of the technical features of the present invention and are not intended to limit the scope of the present invention. Any changes or arrangements that can be easily accomplished by those skilled, without departing from the technical principles and spirit of the present invention are within the scope of the present invention. Accordingly, the scope of the present invention is set forth in the appended claims.

What is claimed is:

1. A composite material for promoting wound healing which consists of a hydrogel and a compound that promotes wound healing, wherein the hydrogel is a reaction product of components consisting of hydrophilic monomers, a cross-linking agent, a metal silicate and water, wherein the compound that promotes wound healing is distributed in the hydrogel, wherein the water content of the hydrogel is >40.

2. The composite material of claim 1, wherein the hydrophilic monomers are from 8 to 80% by weight based on the weight of the hydrogel.

3. The composite material of claim 1, wherein the cross-linking agent comprises N,N'-methylenebisacrylamide, ethylene glycol dimethacrylate, polyethylene glycol diacrylate, tetraethylene glycol dimethacrylate, triethylene glycol dimethacrylate, polyethylene glycol dimethacrylate, trimethylpropanetrimethacrylate, ethylene methacrylate, ethylenediamine dimethyl acrylamide, glycerol dimethacrylate, diethylene glycol dimethacrylate, divinyl benzene or a combination thereof.

4. The composite material of claim 1, wherein the cross-linking agent is from 0.1 to 20% by weight based on the weight of the hydrogel.

5. The composite material of claim 1, wherein the metal silicate is from 2 to 80% by weight based on the weight of the hydrogel.

6. The composite material of claim 1, wherein the compound that promotes wound healing comprises collagen, hyaluronic acid, gelatin, a growth factor, a cytokine, an alginate, silver ions, chitosan or a combination thereof.

7. The composite material of claim 1, wherein the compound that promotes wound healing is from 0.01 to 20% by weight based on the total weight of the hydrogel.

8. The composite material of claim 1, which is further bonded with a film, wherein the film has a two-sided structure, wherein one side is a bonding surface which is bonded with the composite material, and the surface area of the film is greater than the surface area of the composite material.

9. The composite material of claim 1, wherein the hydrophilic monomers comprise acrylic acid having a double bond or a derivative thereof, acrylamide or a derivative thereof, 2-acrylamido-2-methylpropane sulfonic acid or a salt thereof, polyethylene glycol or a derivative thereof, or a combination thereof.

* * * * *